United States Patent [19]

Tovey et al.

[11] Patent Number: 5,454,791
[45] Date of Patent: Oct. 3, 1995

[54] TROCAR WITH TISSUE PENETRATION PRESSURE INDICATOR

[75] Inventors: H. Jonathan Tovey, Milford, Conn.; Sidney D. Autry, Bellingham, Wash.

[73] Assignee: United States Surgical Corporation, Norwalk, Conn.

[21] Appl. No.: 116,788

[22] Filed: Sep. 7, 1993

[51] Int. Cl.⁶ .................................................. A61M 5/178
[52] U.S. Cl. ........................... 604/118; 604/164; 604/264
[58] Field of Search ..................................... 604/164, 264, 604/118, 117

[56] References Cited

U.S. PATENT DOCUMENTS

| | | | |
|---|---|---|---|
| 2,623,521 | 12/1952 | Shaw . | |
| 3,763,860 | 10/1973 | Clarke . | |
| 4,162,673 | 7/1979 | Patel | 604/51 |
| 4,175,567 | 11/1979 | Patel | 604/51 |
| 4,186,750 | 2/1980 | Patel | 604/272 |
| 4,215,699 | 8/1980 | Patel | 604/272 |
| 4,254,762 | 3/1981 | Yoon . | |
| 4,299,230 | 11/1981 | Kubota . | |
| 4,356,826 | 11/1982 | Kubota . | |
| 4,535,773 | 8/1985 | Yoon | 604/158 |
| 4,808,168 | 2/1989 | Warring | 604/158 |
| 4,940,458 | 7/1990 | Cohn | 604/51 |
| 4,944,724 | 7/1990 | Goldberg et al. | 604/118 |
| 5,066,288 | 11/1991 | Deniega | 604/264 |
| 5,139,485 | 8/1992 | Smith et al. | 604/158 |
| 5,209,721 | 5/1993 | Wilk | 604/26 |
| 5,217,441 | 6/1993 | Shichman | 604/164 |
| 5,258,003 | 11/1993 | Ciaglia | 604/264 |
| 5,352,206 | 10/1994 | Cushieri | 604/164 |

FOREIGN PATENT DOCUMENTS

| | | |
|---|---|---|
| 0484725 | 5/1992 | European Pat. Off. . |
| 0520296 | 12/1992 | European Pat. Off. . |
| 1616107 | 4/1971 | Germany . |
| 536677 | 1/1977 | U.S.S.R. . |

OTHER PUBLICATIONS

Derwin English Language Abstract of German Publication No. DT 2919-390 (Nov. 1980).

*Primary Examiner*—John G. Weiss

[57] ABSTRACT

The present invention relates to a trocar and method for penetrating body tissue. The trocar includes an obturator assembly and a cannula assembly. The obturator assembly has an obturator shaft with a distal end portion adapted to penetrate body tissue and at least one channel extending between a proximal end portion of the shaft and the distal end portion. A pressure indicating system is positioned at the proximal end of the shaft and is provided to respond to the passage of gases through the channel and provide a visual indication when the distal end has penetrated the body tissue. A safety system is associated with the obturator shaft and responsive to gas pressure to shield the distal end portion of the shaft after penetration of the body tissue.

8 Claims, 7 Drawing Sheets

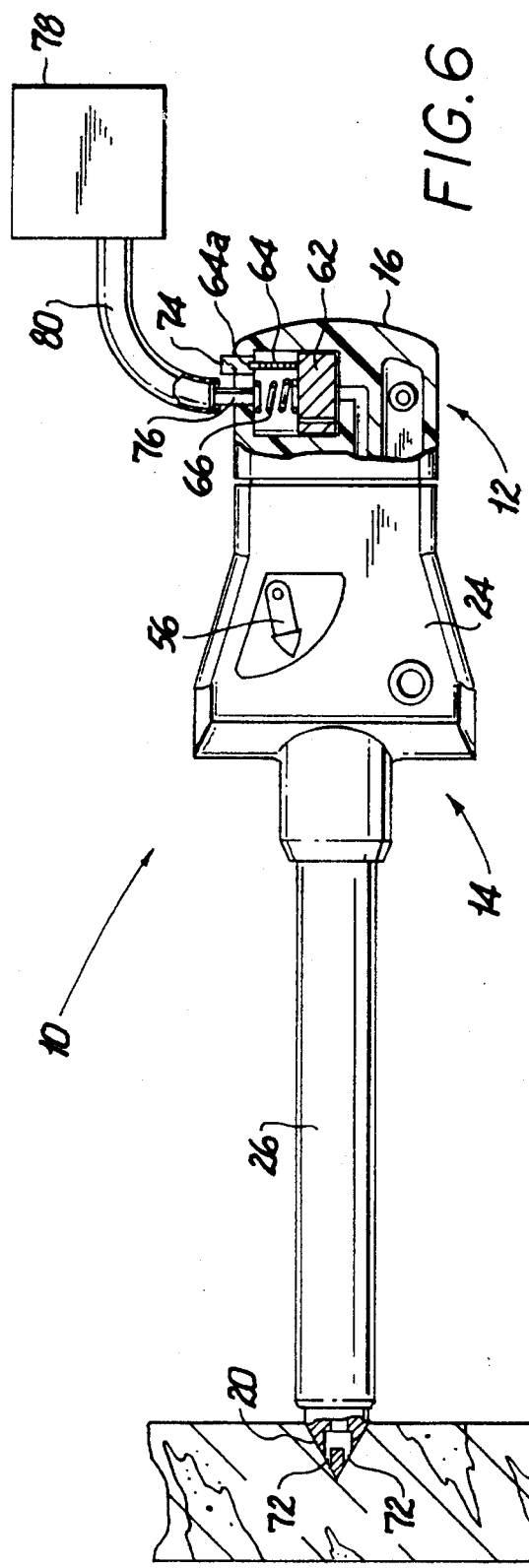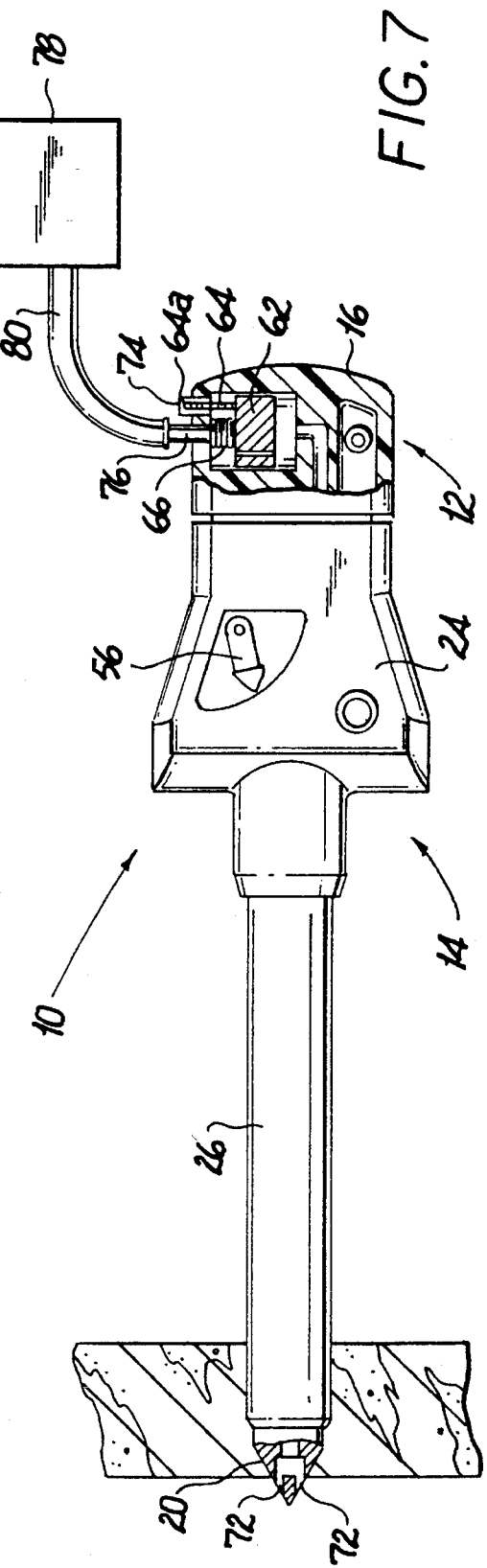

TROCAR WITH TISSUE PENETRATION PRESSURE INDICATOR

BACKGROUND OF THE INVENTION

1. Field of the Invention

The present invention relates to an apparatus for penetrating body tissue. More particularly, the present invention relates to a trocar assembly having a gas pressure system which connects to a gas pressure source to provide an indication when the trocar penetrates the body tissue or to actuate safety means.

2. Description of the Related Art

Endoscopic surgical procedures, that is, surgical procedures performed through tubular sleeves or cannulas, have been utilized for many years. Initially, endoscopic surgical procedures were primarily diagnostic in nature. More recently as endoscopic technology has advanced, surgeons are performing increasingly complex and innovative endoscopic surgical procedures. In endoscopic procedures, surgery is performed in any hollow viscus of the body through small incisions or through narrow endoscopic tubes (or cannulas) inserted through small entrance wounds in the skin. In laparoscopic procedures surgery is performed in the interior of the abdomen.

Laparoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues and vessels far removed from the incision, thereby requiring that any instruments used in such procedures be both long and narrow.

Typically, after the surgical region is insufflated, trocars are used to puncture the body cavity and provide the above noted cannula used during endoscopic procedures. Generally, trocars used during such procedures include a stylet having a sharp tip for penetrating the body cavity and protective tubes positioned over the tip to protect a patient or surgeon from inadvertent contact with the tip. An example of a typical trocar is described in, commonly assigned, U.S. Pat. No. 4,601,710 to Moll. The trocars typically utilize mechanical designs to achieve the desired protective movement of the tube and/or stylet.

One other type of trocar used to puncture the body cavity has a tip which retracts into the cannula. See commonly assigned U.S. Pat. No. 5,116,353 to Green.

Another type of trocar is described in European Patent Application No. 0 484 725. That trocar has a hollow shaft and a tip at a distal end portion of the hollow shaft formed as a window made from a suitable transparent material, such as glass quartz or glass plexiglass. An optic guide and a fiber optic lighting unit are fed to the tip through the hollow shaft. Typically, the optic includes fiber optic light guides which are fed through the hollow shaft to the tip. The optic ends at an axial distance behind the vertex point of the tip so that the optic illuminates the entire lateral surface of the conical window for observation purposes. In this configuration, the operator has a view of the structures that may be penetrated when inserting the instrument. Thus, the operator can, for example, detect blood vessels before they are encountered by the tip of the instrument and avoid them. More particularly, the operator can observe the distal end of the tip during and after complete penetration of the peritoneum so that the subjacent vessels and structures of the peritoneum are safely negotiated.

The present invention, on the other hand, provides a new and different apparatus and method for detecting penetration of the peritoneum or other body portions with a trocar assembly.

SUMMARY OF THE INVENTION

The present invention relates to a trocar having an obturator assembly and a cannula assembly. The obturator assembly includes an obturator shaft having a distal end portion adapted to penetrate body tissue and at least one channel extending between a proximal end portion of the shaft and the distal end portion. Pressure indicating means responsive to the passage of gases through the channel is operatively positioned in communication with the shaft and provides an indication when the distal end portion of the shaft has penetrated the body tissue. In the preferred embodiment, the trocar of the present invention also includes means connected to the pressure chamber for facilitating a connection between the pressure chamber and an external pressure source. However, one skilled in the art will recognize that an internal positive gas pressure source, such as a $CO_2$ cartridge may be utilized.

Preferably, the pressure indicating means includes a pressure chamber positioned at the proximal end portion of the shaft and has a portion thereof connected to the channel. A piston is slidably positioned within the pressure chamber and is movable between a normal position and an indicating position. Biasing means is provided to move the piston to the normal position when gas is not flowing through the channel.

An indicating system may also be positioned within the chamber which is responsive to movement of the piston to provide a surgeon with a visual indication when the piston moves to the indicating position. Preferably, the pressure chamber includes a viewing window which permits observation of at least a portion of the pressure chamber and the indicating means includes an indicating arm which has one end secured to the piston and a free end which can be viewed from the viewing window.

In an alternate embodiment, the trocar of the present invention has an obturator housing with a gas pressure chamber positioned therein, an obturator shaft extending from the housing and an obturator tip secured to a distal end of the obturator shaft. The obturator shaft in combination with the obturator tip has at least one passageway extending therethrough. The at least one passageway extends through the obturator shaft and has one end operatively connected to the gas pressure chamber.

The trocar also includes a cannula housing having a passageway extending therethrough adapted to receive the obturator shaft. A hollow cannula sleeve is secured to the cannula housing so that the passageway of the housing is in cooperative alignment with the opening in the hollow cannula sleeve.

A pressure indicating system is positioned within the gas pressure chamber and is provided to indicate when the obturator tip has penetrated body tissue. Preferably, the pressure indicating system is responsive to the passage of gases through the at least one passageway within the obturator shaft and the obturator tip and the gas pressure chamber.

The present invention also includes a method for indicating the penetration of body tissue by pressure indication. Preferably, an apparatus for penetrating body tissue is provided which has a handle member with a gas pressure chamber positioned therein, and a shaft member having a longitudinal bore therethrough. One end of the shaft is connected to a distal end of the handle member. The longitudinal bore in the shaft is operatively connected with the gas pressure chamber so as to facilitate the passage of gases therethrough.

The apparatus also includes a pressure indicating system positioned within the gas pressure chamber with indication means for indicating when a free end of the shaft member has penetrated the body tissue. Generally, the pressure indicating system is responsive to the passage of gases through the gas pressure chamber. The method of the present invention also includes the following steps: supplying a gas pressure source to the pressure indicating system and penetrating body tissue with the shaft member such that, after penetration, the indicator means is activated.

The present invention further includes a trocar having a cannula assembly and an obturator assembly. The obturator assembly includes an obturator housing and an obturator shaft which has a distal end portion configured to penetrate body tissue. A safety member is associated with the obturator shaft and movable between a safety position and a retracted position. Movement of the safety member is initiated by gas pressure so that after the body tissue is penetrated the safety member shields the distal end portion of the shaft.

BRIEF DESCRIPTION OF THE DRAWINGS

The preferred embodiments of the invention are described hereinbelow with reference to the drawings wherein:

FIG. 6 is a side elevational view in partial cross-section of the trocar assembly of FIG. 1 without the stopcock, and illustrating partial penetration of the trocar assembly through the body tissue and the piston in a normal position;

FIG. 7 is a side elevational view similar to FIG. 6, illustrating sufficient penetration of the obturator tip to cause the piston to move to an indicating position.

DETAILED DESCRIPTION OF THE PREFERRED EMBODIMENTS

The apparatus of the present invention is provided to penetrate body tissue, e.g., the abdominal wall, and to provide an indication to the physician that the body tissue has been penetrated. In the preferred embodiment, the apparatus is a trocar 10 having an obturator assembly 12 and a cannula assembly 14.

Figure 1:
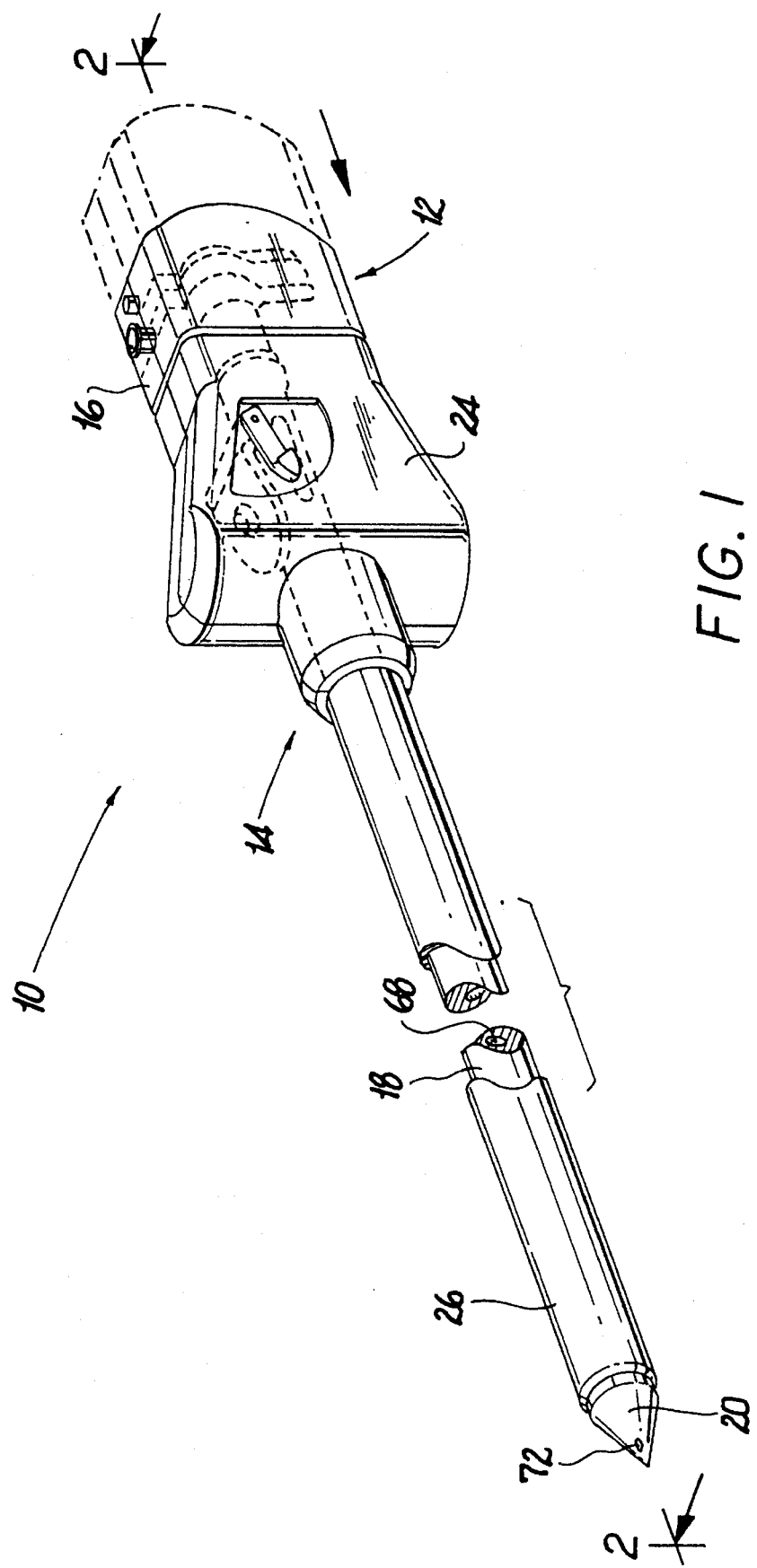
FIG. 1 is a perspective view in partial cut-away of an exemplary trocar assembly configured in accordance with the present invention.
Figure 2:
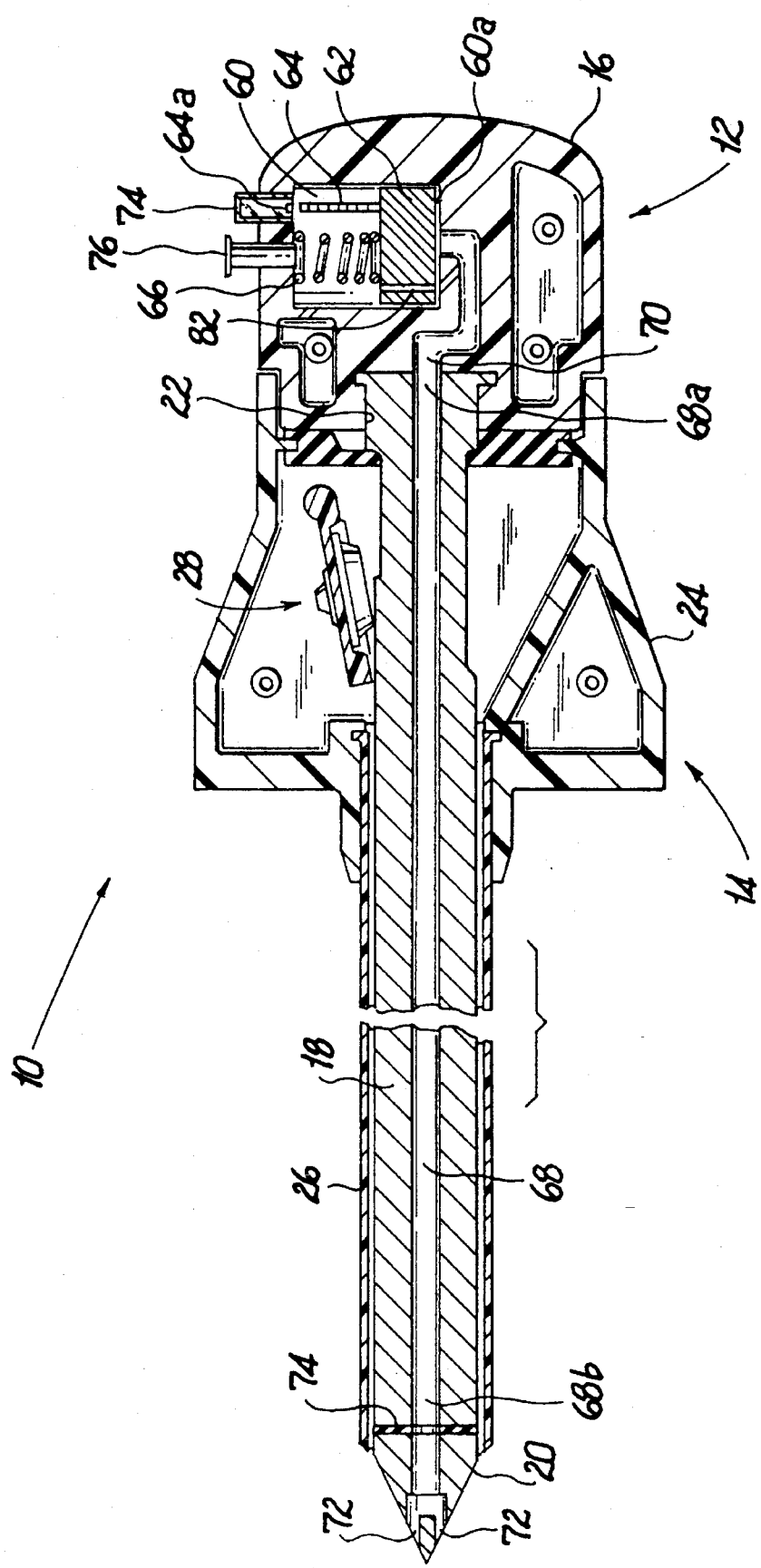
FIG. 2 is a cross-sectional view of the trocar assembly of FIG. 1 taken along line 2—2 and illustrating a gas passage system connected to a gas pressure chamber.

Referring to FIGS. 1 and 2, the obturator assembly includes obturator housing 16, obturator shaft 18, and obturator tip 20. The proximal end of obturator shaft 18 is secured within aperture 22 of obturator housing 16 so that the obturator shaft extends outwardly from the obturator housing, and obturator tip 20 is secured to or formed at the distal end of shaft 18, as shown in FIG. 2.

Cannula assembly 14 includes cannula housing 24 and cannula sleeve 26 which is secured to the cannula housing and extends outwardly therefrom. Cannula housing 24 is configured and dimensioned to interfit with obturator housing 16, as shown in FIG. 1, so that obturator shaft 18 slides within cannula sleeve 26 when the two assemblies are interfitted.

Figure 3:
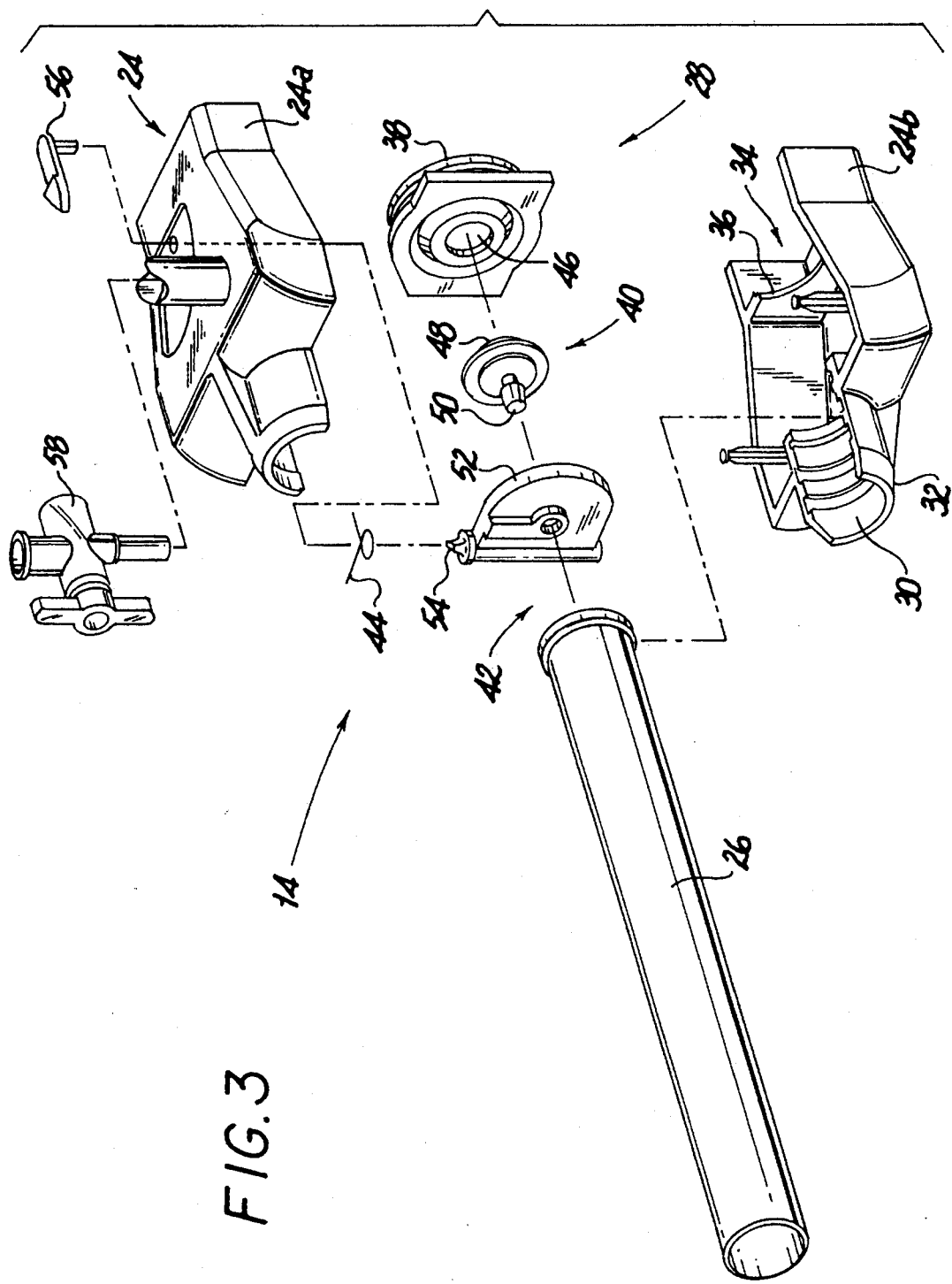
FIG. 3 is a perspective view of the cannula assembly of FIG. 1 with parts separated, illustrating the cannula housing, the cannula sleeve and a valve system.

Generally, as shown in FIG. 3, cannula housing 24 includes a top half section 24a and a bottom half section 24b suitably attached by ultrasonic welding, adhesives, or the like. However, cannula housing 24 may also be of monolithic construction. Preferably, cannula housing 24 has an open interior for mounting valve system 28. Cannula housing 24 also includes at least two openings, a first opening 30, defined by flange 32 which is formed at the distal end of housing 24, and a second opening 34, defined by flange 36 which is formed at the proximal end of housing 24. The first opening 30 permits rigid securement of the proximal end of cannula sleeve 26, and the second opening 34 is positioned in aligned communication relative with the first opening.

The valve system 28 is provided to maintain a gas tight seal within the cannula housing and will be described with reference to FIG. 3. Valve system 28 includes valve seat 38, valve plug 40, valve arm 42 and biasing spring 44. Valve seat 38 is configured and dimensioned for mounting in flange 36 in cannula housing 24. Valve seat 38 defines an aperture 46 extending therethrough which communicates with the first and second openings, 30 and 34 respectively, and is positioned in alignment therewith. Valve plug 40 includes front face portion 48 and stem portion 50 which when secured to valve arm 42 provides a sealed engagement with valve seat aperture 46 in valve seat 38. Valve arm 42 includes valve plate 52 and post 54 and is pivotally mounted within cannula housing 24 via post 54. Biasing spring 44 is positioned on post 54 and within the interior wall of cannula housing 24 to bias valve plug 40 toward a position of engagement with valve seat 38 to effect a gas tight seal. A more detailed description of the valve system described herein and its operation, is provided in, commonly assigned, U.S. Pat. No. 4,943,280 to Lander, which is incorporated herein by reference.

Cannula assembly 14 also includes desufflation lever 56 which is pivotally secured to cannula housing 24 and is provided to manually actuate valve arm 42 for gas desufflation through the cannula assembly. Stopcock type valve 58 is mounted to cannula housing 24 to permit selective insufflation or desufflation of the body cavity prior to performing the surgical procedures.

The indicator portion of trocar 10 will now be described with reference to FIGS. 2 and 4. Generally, the indicator portion of the trocar assembly of the present invention is responsive to the flow of gas through obturator assembly 12 and provides a surgeon with a visual indication that the obturator assembly has penetrated body tissue and entered a body cavity. Preferably, gas pressure chamber 60 is positioned or formed within obturator housing 16 and includes piston 62, indicator arm 64 and spring 66. Channel 68 extends through obturator shaft 18, as shown, and has a proximal end 68a aligned with channel 70 of obturator housing 16. Air ducts 72 pass through obturator tip 20 and are aligned to coincide with the distal end 68b of channel 68 to allow air or other gases to pass through ducts 72 to channel 68. In instances where obturator tip 20 is secured to obturator shaft 18, seal member 74 is positioned between the distal end of obturator shaft 18 and obturator tip 20 to maintain the air pressure within channel 68.

Referring again to FIGS. 2 and 4, piston 62 is slidably positioned within gas pressure chamber 60 and is movable between a normal position and an indicating position. Preferably, spring 66 biases piston 62 toward base 60a of chamber 60 into the normal position. The normal position, shown in FIG. 2, is the position of the indicator arm 64 when it is not visible through viewing window 74. In the indicating position, shown in FIG. 4, piston 62 moves away from base 60a to a point where free end 64a of indicator arm 64 may be observed through window 74 of chamber 60. Connector port 76 extends through obturator housing 16 and is connected to chamber 60. Connector port 76 provides an external connection between the trocar of the present invention and an external source of either positive or negative gas pressure.

Figure 5:
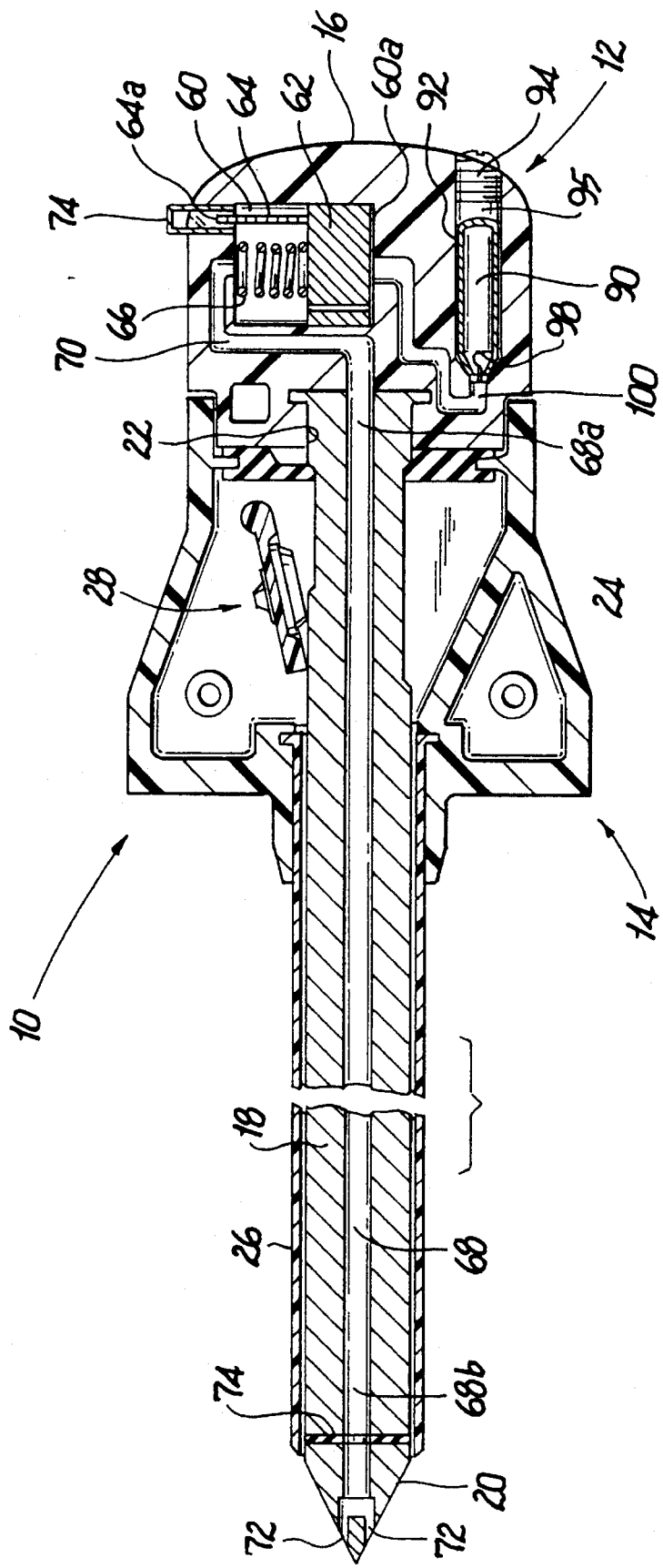
FIG. 5 is a cross-sectional view similar to FIG. 4 and illustrating a positive gas source within the trocar assembly.

Referring to FIG. 5, an alternative embodiment of the indicator portion of the present invention is shown. In this embodiment a $CO_2$ cartridge is utilized to provide a positive source of gas. Cartridge 90 is secured within cartridge chamber 92 by threaded cover 94. Preferably, cover 94 includes resilient member 95 which engages cartridge 90 and maintains the gas pressure within cartridge chamber 92. Pin 98 is provided to puncture cartridge 90 when cover 94 is threaded in chamber 92 and gas from the cartridge passes to pressure chamber 60 via channel 100. In this configuration, spring 66 normally biases piston 62 toward the normal position. When tip 20 penetrates the body tissue, gas pressure from cartridge 90 causes piston 62 to move toward the indicating position.

Figure 4:
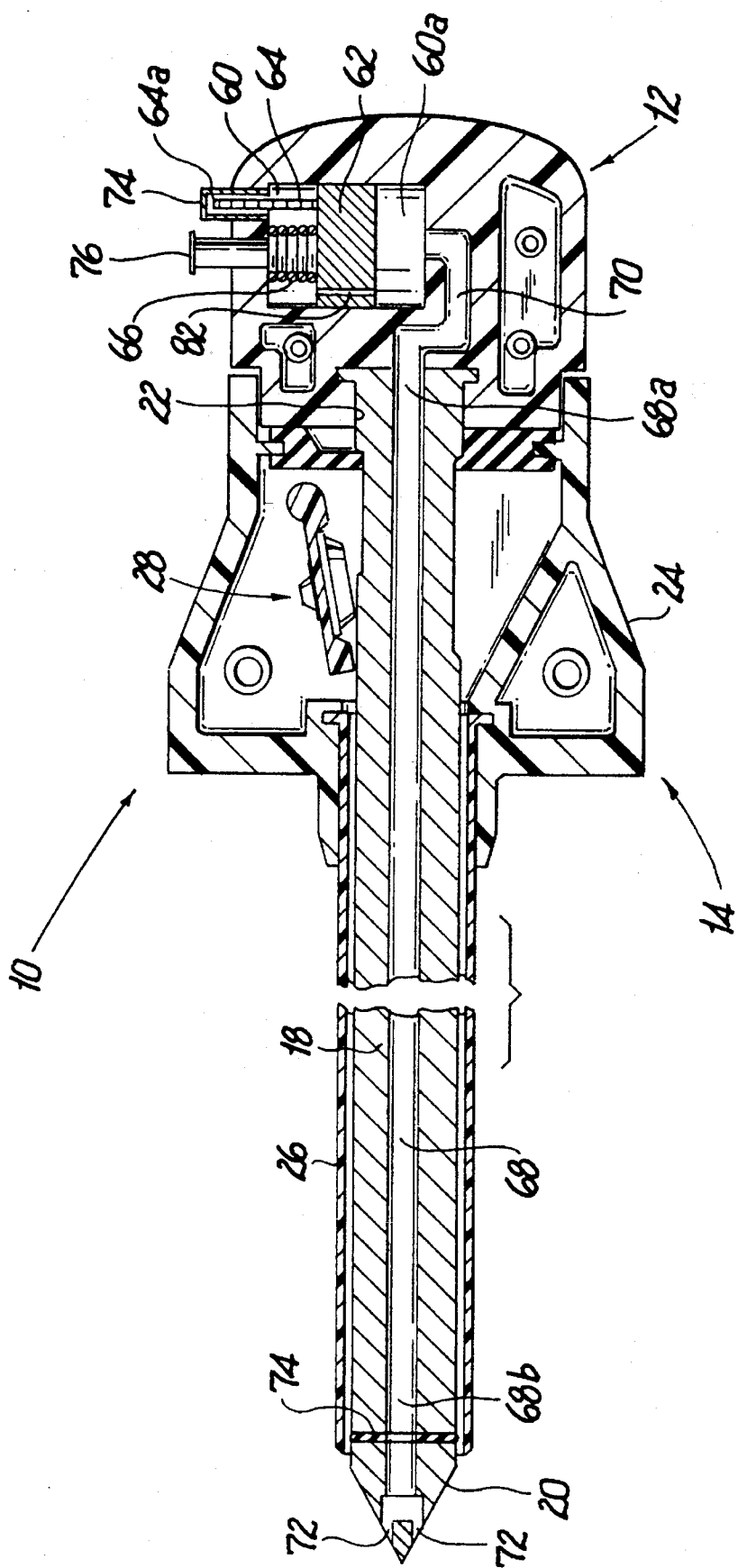
FIG. 4 is a cross-sectional view similar to FIG. 2 and illustrating an indicator arm within the gas pressure chamber which is visible through the viewing window.

In operation of the embodiment of FIGS. 1, 2 and 4, a source of negative gas pressure, i.e., vacuum source 78, is connected to connector port 76 via hose 80 or like member, causing air or other gases to flow through air ducts 72 of obturator tip 20 and channel 68 of obturator shaft 18. In the embodiment of FIG. 5, pressure from the gas of cartridge 90 pushes against piston 62. As a result in both embodiments, a differential pressure is created across piston 62 causing spring 66 to compress and piston 62 to move to the indicating position. Airflow is indicated by free end 64a of indicator arm 64 which extends into window 74 of gas pressure chamber 60, as shown in FIG. 4.

When the openings associated with air ducts 72 engage the body tissue, e.g., as shown in FIG. 6, the airflow through ducts 72 and channel 68 is inhibited. As a result, the differential pressure across piston 62 is equalized by bleed hole 82 extending through piston 62. Equalization of the pressure across piston 62 allows the biasing force of spring 66 to move piston 62 to the normal position, as shown. As noted above, in the normal position, free end 64a of indicating arm 64 is no longer visible through window 74, indicating no airflow through ducts 72.

Once obturator tip 20 penetrates the body tissue to the point where the openings of air ducts 72 are no longer engaged with the body tissue, shown in FIG. 7, the airflow through ducts 72 and channel 68 is restored. Restoration of the airflow causes piston 62 to again move to the indicating position, as described above, so as to provide a surgeon with an indication when the obturator has penetrated the body tissue and entered a body cavity.

Figure 8:
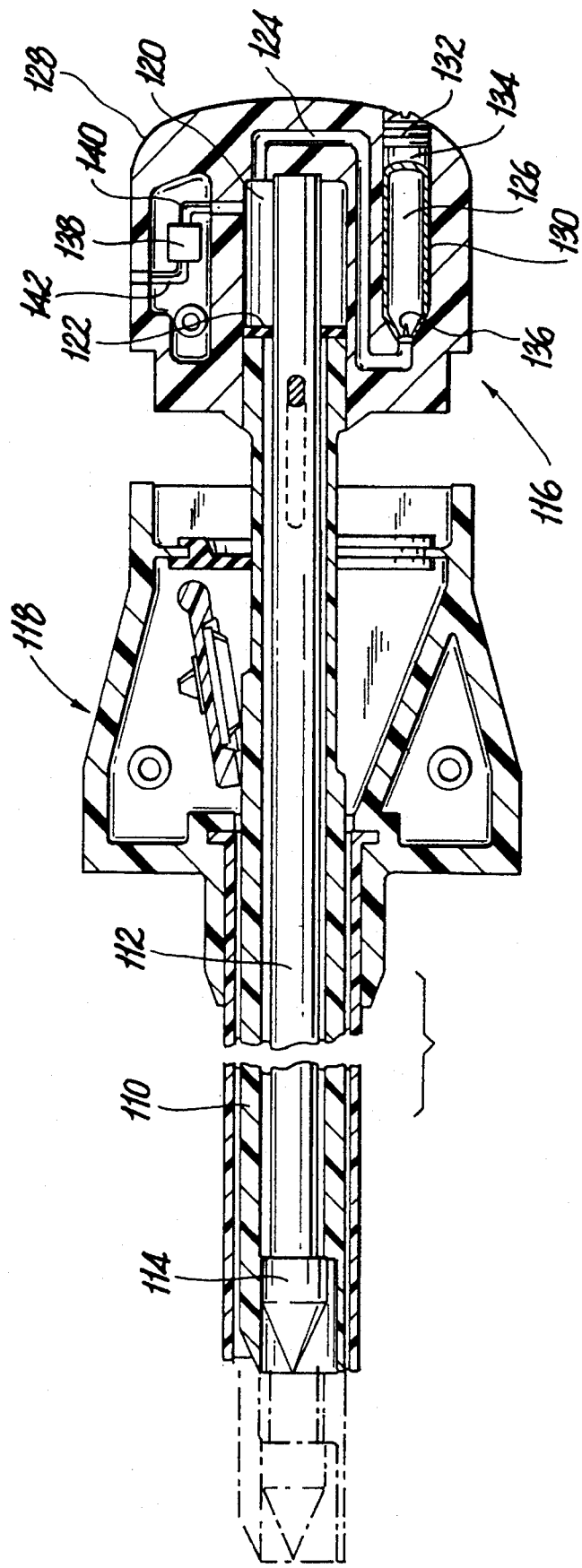
FIG. 8 is a top cross-sectional view of a trocar assembly utilizing gas pressure to move a protective tube.

The trocars noted above in the description of the related art, rely on protective tubes to prevent inadvertent contact between the tip and body tissue. These trocars utilize intricate mechanical designs to achieve the desired protective movement of the tube. In an alternative embodiment, gas pressure may be used to achieve the desired protective movement of the tube, as will be described below. An exemplary embodiment of the utilization of gas pressure to move the tube is shown in FIG. 8. As is common with most trocar assemblies, an obturator assembly 116 is configured to interfit with a cannula assembly 118. A more detailed description of the interrelation between the two assemblies and the operation of the trocar assembly is described in commonly assigned U.S. Pat. No. 4,943,280, to Lander, which is incorporated herein by reference.

In this embodiment, protective tube 110 is positioned concentrically around obturator shaft 112 and is movable between a safety position which minimizes the exposure of obturator tip 114 and a retracted position where tip 114 is exposed.

The proximal end of protective tube 110 is slidably positioned within biasing chamber 120. Seal member 122 is secured to the proximal end of tube 110 and is provided to maintain a gas tight seal within the chamber. In this exemplary embodiment, the gas pressure source is a $CO_2$ cartridge 126 positioned within obturator housing 128. Cartridge 126 is secured within cartridge chamber 130 by threaded cover 132. Preferably, cover 132 includes resilient member 134 which engages cartridge 126 and maintains the gas pressure within cartridge chamber 130. Pin 136 is provided to puncture cartridge 126 when cover 132 is threaded into chamber 130 and gas from cartridge 126 is passed to biasing chamber 120 via channel 124. Relief valve 138 is operatively connected to chamber 120 via channel 140 and has relief vent 142 passing through obturator housing 128.

In operation, gas pressure from cartridge 126 moves protective tube 110 to the protective position, as shown in FIG. 8. Relief valve is closed to maintain the gas pressure. When penetrating the body tissue, tube 110 moves proximally within chamber 120. Proximal movement of the tube causes the gas pressure within the chamber 120 to increase. In some instances the pressure within the chamber may increase to a level where tube 110 is prevented from further proximal movement. To compensate for the increased pressure, relief valve 138 opens when the pressure within the chamber reaches a predetermined level, thus allowing further proximal movement of the tube.

When the body tissue is penetrated the back-pressure within the chamber caused by tube 110 ceases. Relief valve 138 then closes and cartridge 126 increases the pressure within chamber 120 to move tube 110 distally to the protective position.

It will be understood that various modifications can be made to the embodiments of the present invention herein disclosed without departing from the spirit and scope thereof. For example, various sizes of the instrument are contemplated, as well as various types of construction materials. Also, various modifications may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. A trocar having an obturator assembly for penetrating body tissue and including structure activated by gas pressure for achieving protective movement of the obturator assembly after penetration, and a cannula assembly, said obturator assembly comprising:

an obturator shaft having a distal end portion adapted to penetrate body tissue and configured to conduct gas through said distal end portion;

a pressure chamber having at least a portion thereof in aligned communication with said portion of said shaft configured to conduct gas;

an integral gas pressure source in operative communication with said pressure chamber;

a piston slidably positioned within said pressure chamber, said piston being movable between a normal position and an indicating position;

biasing means for moving said piston to said normal position; and indicating means for providing a surgeon with a visual indication when said piston moves to said indicating position.

2. The trocar according to claim 1, wherein said pressure chamber includes a viewing window which permits observation of at least a portion of said pressure chamber.

3. The trocar according to claim 1, wherein said indicating means comprises an indicating arm having one end secured to said piston and a free end which can be viewed from said viewing window.

4. The trocar according to claim 1, wherein said integral pressure source comprises a $CO_2$ cartridge.

5. The trocar according to claim 1, wherein said cannula assembly comprises a cannula housing having a hollow cannula sleeve secured thereto and extending outwardly therefrom, said cannula housing and said sleeve being configured to coaxially align with said obturator shaft.

6. The trocar according to claim 5, wherein said obturator assembly further comprises an obturator housing positioned at a proximal end of said obturator shaft, and at least a portion of said cannula housing is configured and dimensioned to interfit with at least a portion of said obturator housing.

7. A trocar having a cannula assembly and an obturator assembly for penetrating body tissue, said obturator assembly including structure activated by gas pressure for achieving protective movement of the obturator assembly after penetration, said obturator assembly comprising:

an obturator shaft having a distal end portion adapted to penetrate body tissue; and a protective tube coaxially aligned with said obturator shaft and movable between a protective position wherein said distal end portion of said obturator shaft is within said protective tube and a retracted position wherein said distal end portion of said obturator shaft is exposed, said protective tube being initiated to move to said protective position in response to gas pressure.

8. A method for indicating the penetration of body tissue by pressure indication, comprising:

positioning a distal end portion of a gas conductive obturator shaft against the body tissue;

connecting a gas pressure cartridge to a pressure chamber having at least a portion thereof in communication with said gas conductive obturator shaft; and penetrating the body tissue at least with said distal end portion of said gas conductive obturator shaft such that after penetration, gas pressure supplied by said cartridge and within said pressure chamber changes and a pressure indicator positioned within said pressure chamber moves to an indicating position viewable through a viewing window in said pressure chamber.

* * * * *